United States Patent [19]

Brown

[11] Patent Number: 4,795,821

[45] Date of Patent: Jan. 3, 1989

[54] OPTICALLY ACTIVE BORINIC ESTERS AND KETONES

[75] Inventor: Herbert C. Brown, West Lafayette, Ind.

[73] Assignee: Aldrich-Boranes, Inc., Milwaukee, Wis.

[21] Appl. No.: 902,177

[22] Filed: Aug. 29, 1986

[51] Int. Cl.$^4$ ............................ C07F 5/00; C07F 5/04
[52] U.S. Cl. .................................................. 558/298
[58] Field of Search ........................................ 558/298

[56] References Cited

U.S. PATENT DOCUMENTS

| 2,835,693 | 5/1958 | Buls et al. | 558/298 |
| 2,862,952 | 12/1958 | Groszos | 558/298 |
| 2,884,441 | 4/1959 | Groszos | 558/298 |
| 3,027,396 | 3/1962 | Willcockson | 558/298 |
| 3,036,111 | 5/1962 | Willcockson | 558/298 |

FOREIGN PATENT DOCUMENTS

| 668060 | 8/1963 | Canada | 558/298 |
| 680442 | 2/1964 | Canada | 558/298 |
| 684755 | 4/1964 | Canada | 558/298 |
| 856856 | 12/1960 | United Kingdom | 558/298 |
| 929656 | 6/1963 | United Kingdom | 558/298 |
| 936373 | 9/1963 | United Kingdom | 558/298 |

*Primary Examiner*—Paul F. Shaver
*Attorney, Agent, or Firm*—Joyce R. Niblack; Robert L. Niblack

[57] ABSTRACT

A process for synthesizing an optically pure ketone comprising the steps of: treating an appropriate optically pure boronic ester with an organolithium compound at $-78°$ C. to obtain the "ate" complex, separating the optically pure borinic ester from the complex and converting said borinic ester into an optically pure ketone represented by the formulae:

$$R^*COR^1 \text{ and } R^*COC\equiv CR^1$$

wherein $R^*$ is a chiral organyl moeity and $R^1$ is an achiral organyl moeity.

9 Claims, No Drawings

OPTICALLY ACTIVE BORINIC ESTERS AND KETONES

BACKGROUND OF THE INVENTION

This invention relates to novel optically pure borinic esters represented by the formula $R^*R^1BOR^2$, wherein $R^*$ is an aliphatic, alicyclic or heterocyclic chiral moiety, $R^1$ is an aliphatic, alicyclic, aromatic, heterocyclic or alkynyl achiral moeity, introduced via an organolithium compound, $R^1Li$, and $R^2$ is a simple organyl group such as lower alkyl. The present invention further relates to a process of preparing these optically pure borinic esters and their conversion by reaction with α,α-dichloromethylmethylether (DCME) in the presence of lithium tert-butoxide or lithium triethylcarboxide, followed by oxidation with hydrogen peroxide in pH 8 phosphate buffer solution, to optically pure α-chiral acyclic ketones represented by the formula

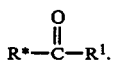

Borinic esters are attractive organoborane intermediates in carbon-carbon bond forming reactions. No loss of alkyl groups occur and such 1,2-migrations are known to proceed with complete retention of stereochemistry and configuration of the migratory carbon nucleus. Chiral borinic esters represented by the formula $R^*R^1BOR^2$ wherein $R^*$ is chiral (an optically active organyl group, with boron attached directly to the optically active center) and $R^1$ is obtained by hydroboration and converted into optically active ketones by reaction of the borinic esters with α,α-dichloromethyl ether (DCME) and lithium triethylcarboxide, followed by alkaline hydrogen peroxide oxidation [H. C. Brown, P. K. Jadhav and M. C. Desai, *Tetrahedron*, 40, 1325 (1984)].

However, alkaline hydrogen peroxide has been observed to cause racemization and epimerization in the conversion of optically active borinic esters to ketones. Also, the borinic esters and therefore the ketones are restricted to groups which are obtainable by hydroboration. Finally, the process is a complex one, requiring a number of steps.

In addition, acyl(1-alkynyl)borinic esters have been prepared in low yield and purity by the reaction of an alkynylboronic ester and Grignard reagent, followed by aqueous acidic workup [D. S. Matteson and K. Peacock, *J. Organomet. Chem.*, 2, 192 (1964)].

The present invention overcomes the disadvantages of the prior art, provides novel achiral and chiral alkyl-(1-alkynyl)borinic esters, $RB(C≡CR^1)OR^2$ and $R^*B(C≡CR^1)OR^2$, and provides a novel process for preparing achiral and chiral ketones employing the novel intermediates.

SUMMARY OF THE INVENTION

The present invention provides novel achiral and chiral alkyl-(1-alkynyl)borinic esters represented by the formulae $RB(C≡CR^1)OR^2$ and $R^*B(C≡CR^1)OR^2$ wherein R is an achiral organyl group, $R^*$ is a chiral organyl group, $R^1$ is an aliphatic, alicyclic, aromatic, heterocyclic or alkynyl achiral moiety, and $R^2$ is a simple organyl group.

In addition, the present invention provides a method of producing optically pure borinic esters comprising the steps of reacting an optically pure boronic ester of the formula $R^*B(OR^2)_2$, and an organolithium reagent, $LiR^1$, followed by treatment with a compound selected from the group consisting of ethereal hydrogen chloride, acetyl chloride and chlorotrimethylsilane as follows:

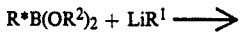

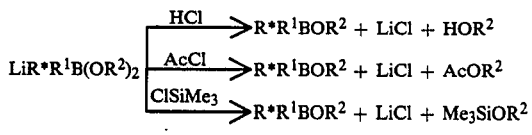

wherein $R^*$, $R^1$ and $R_2$ are as defined above.

When $R^1$ is an aliphatic, alicyclic, aromatic or heterocyclic group, it is advantageous to use either the diisopropyl or trimethylene ester to obtain clean monoalkylated product. This procedure makes readily available a vast number of optically pure borinic esters which are not obtainable by hydroboration.

In addition, this process provides a method for obtaining achiral and chiral alkyl-(1-alkynyl)borinic esters, in pure form, represented by the formulae:

wherein R, $R^*$, $R^1$ and $R^2$ are as defined above, by the reaction of an appropriate boronic ester and a lithium acetylide, followed by treatment with ethereal hydrogen chloride as follows:

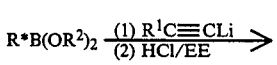

A further embodiment of the present invention resides in the important discovery that these optically pure borinic esters are cleanly converted into optically pure α-chiral ketones by the steps of reacting an optically pure borinic ester represented by the formula $R^*R^1BOR^2$ with α,α-dichlorodimethyl ether (DCME) in the presence of lithium triethylcarboxide, followed by oxidation with hydrogen peroxide in pH 8 phosphate buffer at room temperature according to the following reaction sequence.

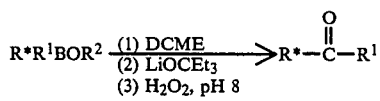

In addition, according to one aspect of the present invention, lithium tert-butoxide can be used in the conversion of optically pure borinic esters, $R^*R^1BOR^2$ (where $R^1$ is not an alkynyl group) into optically pure α-chiral acyclic ketones. This process offers a major advantage in cost and in the isolation of volatile optically pure ketones.

In a further embodiment, for sterically hindered optically pure borinic esters, the conversion to optically pure ketones is best accomplished by oxidation with anhydrous trimethylamine-N-oxide in benzene, represented by the following reaction scheme:

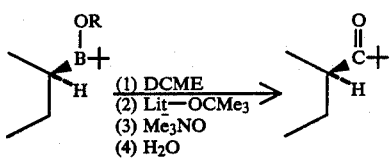

This method of oxidation is general for all sterically hindered systems. Anhydrous trimethylamine-N-oxide is also effective in oxidizing the boronic esters obtained in the reaction of sterically nonhindered borinic esters and DCME in the presence of lithium tert-butoxide or lithium triethylcarboxide according to the following reaction scheme:

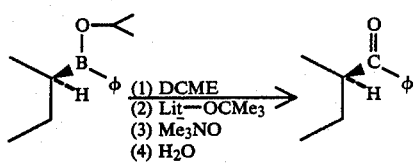

DESCRIPTION OF PREFERRED EMBODIMENTS

As can be seen from the following examples, the processes of the present invention for the synthesis of optically pure borinic esters and their conversion into optically pure α-chiral ketones are widely applicable. Aliphatic, alicyclic, aromatic and heterocyclic organolithium reagents can be used, as well as substituted lithium acetylides.

In the following examples, all glassware was dried at 140° C. for at least 3 h, assembled hot and cooled under a stream of nitrogen. Anhydrous ethyl ether (Mallinckrodt) was stored over 4 Å molecular sieves under nitrogen and used without further purification. The organolithium reagents (methyllithium and phenyllithium) are commercial materials (Aldrich or Alfa). The concentrations were standardized prior to use. DCME (α,α-dichloromethylmethyl ether, Aldrich) was distilled from $CaH_2$ and stored under nitrogen. A stock solution of lithium tert-butoxide in hexane was prepared from n-butyllithium and tert-butanol and was standardized prior to use. The $^1H$ NMR spectra were recorded on a Varian T-60 or XL-200 instrument, relative to tetramethylsilane. $^{13}C$ NMR spectra were scanned on a Varian XL-200, relative to $Me_4Si$. $^{11}B$ NMR were obtained on a Varian FT-80A spectrometer relative to boron trifluoride etherate. Infrared spectra were obtained on a Perkin-Elmer 1420 ratio-recording infrared spectrometer. Mass spectra were obtained on a Finnigan Model 4000 gas chromatograph mass spectrometer. High Resolution Mass Spectra (HRMS) were run on a Kratos MS-50. Optical rotations were measured on a Rudolph Polarimeter Autopol III. Capillary gas chromatographic analyses were carried out with a Hewlett-Packard 5850 chromatograph.

The chiral boronic ester starting intermediates of either (+) or (−) series are readily available in essentially pure optical form. Brown, H. C. et al., *J. Am. Chem. Soc*, 106, 1797 (1984), incorporated by reference herein.

All borinic esters, chiral and achiral, were prepared by the general method of Example 1.

EXAMPLE 1

General Procedure for Preparation of Borinic Esters

To a round bottom flask fitted with a magnetic stirring bar and adaptor is added 25–100 mmol of the boronic ester in 50–200 mL of ether to give an initial concentration of ca. 0.5M. The solution is cooled in a dry ice/acetone bath. An equivalent of alkyllithium is added dropwise via a double-ended needle over a period of 30–45 min. The reaction is stirred for 3 h, then quenched with the addition of an equivalent of hydrogen chloride in ether or with neat acid chloride or chlorotrimethylsilane and warmed to room temperature. The clear ether solution is decanted from the lithium chloride precipitate and combined with the ether washes of the solid. After the ether is removed, either by atmospheric distillation or under reduced pressure, the residual material is distilled at atmospheric or reduced pressure.

EXAMPLE 2

[R]-(1-Methylpropyl)-3'-acetoxy-1'-propoxymethylborane was prepared from [R]-(−)-2-(1-methylpropyl)-1,3,2-dioxaborinane of 99% ee and methyllithium, then quenched with acetyl chloride following the procedure of Example 1. IR$_{\gamma max}$ 17.41 $cm^{-1}$. $^1H$ NMR ($CDCl_3$) δ0.37 (s, 3H), 0.90 (m, 6H), 1.70 (s, 3H), 4.00 (m, 2H), 4.17 (m, 2H).

EXAMPLE 3

[R]-(1-Methylpropyl)-3'-O-trimethylsilyl-1'-propoxymethylborane was prepared from [R]-(−)-2-(1-methylpropyl)-1,3,2-dioxaborinane of 99% ee and methyllithium, then quenched with chlorotrimethylsilane following the procedure of Example 1. $^1H$ NMR ($CDCl_3$) δ0.13 (s, 9H), 0.37 (s, 3H), 0.87 (m, 6H), 1.73 (m, 2H), 3.67 (t, J=6 Hz, 2H), 3.93 (t, J=6 Hz, 2H).

EXAMPLE 4

[R]-(1-Methylpropyl)-3'-O-trimethylsilyl-1'-propoxyphenylborane was prepared from [R]-(−)-2-(1-methylpropyl)-1,3,2-dioxaborane of 99% ee and phenyllithium by the method of Example 1, then quenched with chlorotrimethylsilane. $^1H$ NMR ($CDCl_3$) δ0.13 (s, 9H), 1.10 (m, 6H), 1.87 (quintet, J=6 Hz, 2H), 3.77 (t, J=6 Hz, 2H), 4.17 (t, J=6 Hz, 2H), 7.33 (m, 3H), 7.53 (m, 2H).

EXAMPLE 5

[R]-(1-Methylpropyl)-3'-O-trimethylsilyl-1'-propoxytert-butylborane was prepared from [R]-(−)-2-(1-methylpropyl)-1,3,2-dioxaborinane of 99% ee and tert-butyllithium at −100° C., then quenched with chlorotrimethylsilane following the procedure of Example 1. $^1H$ NMR ($CDCl_3$) δ0.10 (s, 9H), 0.90 (s, 9H), 3.67 (t, J=6 Hz, 2H), 4.13 (t, J=6 Hz, 2H).

EXAMPLE 6

[R]-(1-Ethylbutyl)-3'-O-trimethylsilyl-1'-propoxy-3"-furylborane was prepared by the method of Example 1 from [R]-(−)-2-(1-ethylbutyl)-1,3,2-dioxaborinane of 99% ee and 3-furanyllithium, then quenched with chlorotrimethylsilane. $^1H$ NMR ($CDCl_3$) δ0.10 (s, 9H), 3.70 (m, 2H), 4.23 (m, 2H), 6.52 (m, 1H), 7.40 (m, 1H), 7.70 (m, 1H).

EXAMPLE 7

[1S, 2S]-(trans-2-Methylcyclopentyl)-3'-O-trimethylsilyl-1'-propoxyphenylborane was prepared by the method of Example 1 from [1S, 2S]-(+)-2'-(trans-2-methylcyclopentyl)-1',3',2'-dioxaborinane of 99% ee and phenyllithium, then quenched with chlorotrimethylsilane. $^1$H NMR (CDCl$_3$) δ0.10 (s, 9H), 1.00 (d, J=6 Hz, 3H), 1.77 (m, 8H), 3.67 (t, J=6 Hz, 2H), 4.13 (t, J=6 Hz, 2H), 7.23 (m, 3H), 7.53 (m, 2H).

EXAMPLE 8

[1S,2S]-(trans-2-Phenylcyclopentyl)-3'-O-trimethylsilyl-1'-propoxymethylborane was prepared from [1S,2S]-(+)-2'-(trans)-2-phenylcyclopentyl)-1',3',2'-dioxaborinane of 99% ee, and methyllithium, then quenched with chlorotrimethylsilane by the procedure of Example 1. $^1$H NMR (CDCl$_3$) δ0.10 (s, 9H), 0.30 (s, 3H), 1.73 (m, 10H), 3.73 (m, 4H), 7.17 (bs, 5H).

EXAMPLE 9

[1S,2S]-(trans-2-Phenylcyclopentyl)-3'-O-trimethylsilyl-1'-propoxy-2''-furylborane was prepared by the method of Example 1 from [1S,2S]-(+)-2'-(trans-2-phenylcyclopentyl)-1',3',2'-dioxaborinane of >99% ee and 2-furyllithium, then quenched with chlorotrimethylsilane. $^1$H NMR (CDCl$_3$) δ0.10 (s, 9H), 3.67 (t, J=6 Hz, 2H), 4.23 (t, J=6 Hz, 2H), 6.33 (m, 1H), 6.97 (m, 1H), 7.17 (bs, 5H), 7.57 (m, 1H).

EXAMPLE 10

[S]-(Cyclohex-3-ene)-methylisopropoxyborane was prepared by the method of Example 1 from [S]-cyclohex-3-enediisopropoxyborane of >99% ee and methyllithium. $^1$H NMR (CDCl$_3$) δ0.40 (s, 3H), 1.10 (d, J=6 Hz, 6H), 4.43 (sept. J=6 Hz, 1H), 5.73 (m, 2H).

EXAMPLE 11

[1S,2S]-(trans-2-Methylcyclohexyl)-3'-acetoxy-1'-propoxymethylborane was prepared by the method of Example 1 from [1S,2S]-(+)-2'-(trans-2-methylcyclohexyl)-1',3',2'-dioxaborinane of >99% ee and methyllithium. IR$_{\gamma max}$ 1742 cm$^-$. $^1$H NMR (CDCl$_3$) δ0.50 (s, 3H), 0.47 (d, J=6 Hz, 3H), 1.57 (s, 3H), 3.67 (m, 4H).

EXAMPLE 12

[1S,2S]-exo-Norbornylmethylisopropoxyborane was prepared following the method of Example 1 from [1S,2S]-exonorbornyldiisopropoxyborane of 86% ee and methyllithium. $^1$H NMR (CDCl$_3$) δ0.37 (s, 3H), 1.19 (d, J=6 Hz, 6H), 2.23 (m, 2H), 4.40 (sept. J=6 Hz, 1H).

EXAMPLE 13

[1R,2R,5R,5S]-(3-Isopinocampheyl)-3'-O-trimethylsilyl-1'-propoxymethylborane was prepared following the method of Example 1 from [1R,2R,3R,5S]-(−)-2'-(3-isopinocampheyl)-1',3',2'-dioxaborinane of 99% ee and methyllithium. $^1$H NMR (CDCl$_3$) δ0.01 (s, 9H), 0.47 (s, 3H), 0.87 (d, J=6 Hz, 3H), 1.07 (s, 3H), 1.17 (s, 3H), 3.67 (m, 2H), 4.00 (m, 2H).

EXAMPLE 14

Preparation of sec-Butyl(5-chloro-1-pentynyl)isopropoxyborane

To a tetrahydrofuran (THF) solution of 5-chloro-1-pentynyllithium prepared from 5-chloro-1-pentyne (5.43 g, 53 mmol) and n-butyllithium (20.4 mL, 53 mmol) cooled to −78° C. was added sec-butyldiisopropoxyborane (8.74, 48 mmol) in 48 mL THF. The reaction mixture was stirred at −78° C. for an additional 1 h, then quenched with hydrogen chloride in ethyl ether (15.5 mL, 53 mmol). The cooling bath was removed and the reaction mixture allowed to warm to room temperature. The lithium chloride was allowed to settle and the clear supernatant was decanted via a double-ended needle into a distillation flask. The remaining solid lithium chloride was washed with THF, 2×15 mL, and added to the distillation flask. Volatiles were removed with reduced pressure, followed by high vacuum distillation. Yield: 9.5 g (92%), bp 72°–74° C. (0.1 mm Hg); n$^{20}$D 1.4496; proton NMR (CDCl$_3$) δ4.43 (septet, J=18 Hz, 1H), 3.60 (triplet, J=18 Hz, 2H), 2.47 (triplet, J=18 Hz, 2H), 1.17 (d, J=18 Hz, 6H), 0.87 (m,6H); boron NMR (EE) δ+41.3 ppm (s); mass spectrum (chemical ionization, isobutane), m/e 213 (M+H, 8%). IR (thin film) 2185, 1325 cm$^{-1}$. Anal. Calcd. for C$_{12}$H$_{28}$BCLO: C, 63.06; H, 9.70; B, 4.73. Found: C, 63.14; H, 9.60; B, 4.48.

EXAMPLE 15

Preparation of Phenyl(1-hexynyl)isopropoxyborane

The title compound was prepared following the method of Example 14, using 1-hexynyllithium (64 mmol) prepared from 1-hexyne and n-butyl lithium in ethyl ether (64 mL) and phenyldiisopropoxyborane (11.96 g, 58 mmol) dissolved in ethyl ether (60 mL) and quenched with hydrogen chloride in ethyl ether (18.7 mL, 64 mmol). Yield. 11.2 g (86%), bp 102°–105° C. (0.4 mm Hg); n$^{20}$D 1.5008; proton NMR (CDCl$_3$) δ7.90 (m, 2H), 7.31 (m, 3H), 4.87 (septet, J=18 Hz, 1H), 2.33 (triplet, J=18 Hz, 2H), 1.23 (d, J=18 Hz, 6H), 0.90 (triplet, 3H); boron NMR (CDCl$_3$) δ+36.5 ppm(s); mass spectrum (chemical ionization, isobutene) m/e 229 (M+H, 10%); IR (thin film) 2195, 1324 cm$^{-1}$.

Anal. Calcd. for C$_{15}$H$_{21}$BO: C, 78.97; H, 9.28. Found: C, 78.18; H, 9.27.

EXAMPLE 16 n-Hexyl(3,3-dimethyl-1-butynyl)isopropoxyborane was prepared by adding 2-n-hexyl-diisopropoxyborane (8.35 g, 39 mmol) in ethyl ether (18 mL) to an ethyl ether solution of 3,3-dimethyl-1-butynyllithium (44 mmol in 44 mL of ethyl ether), following the method of Example 14, and quenched with HCl in ethyl ether (12.87 mL, 44 mmol). Yield: 7.2 g (79%), bp 80°–82° C. (0.1 mm Hg); n$^{20}$D 1.4265, boron NMR (ethyl ether) δ+40.6 ppm(s); mass spectrum (chemical ionization, isobutene) m/e 237 (M+H, 7%); IR (thin film) 2186, 1327 cm$^{-1}$. Anal. Calcd. for C$_{15}$H$_{29}$BO: C, 76.23; H, 12.38; B, 4.58. Found: C, 76.35; H, 12.02; B, 4.61.

EXAMPLE 17

Following the procedure of Example 14, 2,3-dimethyl-2-butyl(3',3'-dimethyl-1'-butynyl)-3''-acetoxy-1''-propoxyborane was prepared by adding the dioxaborolane ester (4.52 g, 29 mmol) in ethyl ether (20 mL) to an ethyl ether solution of 3,3-dimethyl-1-butynyllithium (32 mmol in 33 mL ethyl ether), and quenching the reaction with acetyl chloride (2.5 g, 32 mmol). Yield: 6.5 g (79%), bp 96°–98° C. (0.1 mm Hg); n$^{20}$D 1.4436; proton NMR (CDCl$_3$) δ+43.5 ppm(s); mass spectrum (chemical ionization, isobutene) m/e 281 (M+H, <1%), 105 [HO(CH$_2$)$_2$OAc+H, 100%]; IR (thin film) 2189, 1745, 1318 cm$^{-1}$. Anal. Calcd. for C$_{16}$H$_{29}$BO$_3$: C, 68.58; H, 10.43; B, 3.86. Found: C, 69.03; H, 10.07; B, 3.97.

EXAMPLE 18 sec-Butyl(1-octynyl)isopropoxyborane was prepared following the method of Example 12 with sec-butyldiisopropoxyborane (10.79 g, 58 mmol) in ethyl ether (58 mL) and added to a solution of 1-octynyllithium (64 mmol in 64 mL, THF) and quenched with HCl in ethyl ether (18.82 mL, 64 mmol). Yield: 10.1 g (74%), bp 68°-70° C. (0.1 mm Hg); $n^{20}D$ 1.4366; proton NMR (CDCl$_3$) $\delta$4.60 (septet, J=18 Hz, 1H), 2.23 (triplet, 2H), 1.17 (d, J=18 Hz, 6H), 0.87 (m, 9H); boron NMR (CDCl$_3$) $\delta$+41.6 ppm(s); mass spectrum (chemical ionization, isobutee) m/e 237 (M+H, 15%); IR (thin film) 2183, 1324 cm$^1$. Anal. Calcd. for C$_{15}$H$_{29}$BO: C, 76.77; H, 12.38; B, 4.58. Found: C, 76.30; H, 12.39; B, 4.63.

EXAMPLE 19

Preparation of Cyclopentyl(1-octynyl)isopropoxyborane

Cyclopentyldiisopropoxyborane (2.33 g, 37 mmol) in ethyl ether (37 mL) was added to an ethereal solution of 1-octynyllithium (41 mmoL in 41 mL ethyl ether), then quenched with HCl in ethyl ether (12.0 mL, 41 mmol). Workup as described in Example 14 yielded 6.95 g (76%), bp 100°-102° C. (0.1 mm Hg); $n^{20}D$ 1.4557; proton NMR (CDCl$_3$) $\delta$4.63 (septet, J=18 Hz, 1H), 2.23 (triplet, 1H), 1.17 (d, J=18 Hz, 6H), 0.83 (triplet, 3H); boron NMR (EE) $\delta$+41.2 ppm(s); mass spectrum (chemical ionization, isobutene) m/e 249 (M+H), 40%); IR (thin film) 2186, 1344 cm$^{-1}$. Anal. Calcd. for C$_{16}$H$_{29}$BO: C, 77.42; H, 11.78. Found: C, 77.02; H, 11.92.

EXAMPLE 20

Preparation of Methyl(phenylethynyl)isopropoxyborane

The reaction was run following the method of Example 14 using methyldiisopropoxyborane (6.34 g, 44 mmol) in ethyl ether (44 mL) and phenylethynyllithium (4.9 mmol) in ethyl ether (50 mL), then quenched with hydrogen chloride (14.33 mL, 49 mmol). Volatiles were removed under reduced pressure at ambient temperature to yield 7.45 g (91%) of the title product; $n^{20}D$ 1.5290; proton NMR (CDCl$_3$) $\delta$7.23 (m, 5H), 4.73 (septet, J=18 Hz, 1H), 1.23 (d, J=18 Hz, 6H), 0.53 (bs, 3); boron NMR (EE) $\delta$+40.2 ppm(s). Mass spectrum (chemical ionization, isobutene) m/e 187 (M+H, 6%); IR (thin film) 2178, 1326 cm$^{-1}$.

Anal. Calcd. for C$_{12}$H$_{15}$BO: C, 77.46; H, 8.13. Found: C, 76.00; H, 7.69.

EXAMPLE 21

General Procedure for the Preparation of -Chiral Acyclic Ketones

A 500-mL round-bottom flask containing a magnetic stirring bar was capped with a rubber septum and charged with 15 mmol of borinate. Diethyl ether was added (15 mL) and the reaction cooled to 0° C. DCME (22.5 mmol, 2.04 mL) was added, followed by lithium tert-butoxide (30 mmol, 16.2 mL). The ice-bath was removed and the mixture stirred at room temperature 1 h during which time a slightly exothermic reaction developed and a white precipitate formed. The reaction mixture was cooled to 0° C. and pH 8 phosphate buffer solution (45 mmol, 18 mL) added, followed by 30% hydrogen peroxide (45 mmol, 5.1 mL). The ice-bath was removed and the two-phase system stirred 12 h. The phases were separated and the aqueous phase extracted with diethyl ether (2×15 mL), dried over MgSO$_4$ and filtered. Volatiles were removed under reduced pressure, unless otherwise indicated. The residual oil was then distilled bulb-to-bulb. The purity of the ketones, as determined by GC (5% sp 2100 on Chromosorb W, 6 ft×$\frac{1}{8}$ in column), is usually 95%. The chiral ketones were further purified by preparative GC (20% sp 2100 on Chromosorb W, 60-80 mesh, 6 ft×0.5 in).

EXAMPLE 22

[R]-(−)-3-Methylpentan-2-one was prepared from [R]-(−)-(1-methylpropyl)-3′-O-trimethylsilyl-1′-propoxymethylborane by the method of Example 21. The volatiles from this reaction were removed at atmospheric pressure. IR$_{\gamma max}$ 1709 cm$^{-1}$. $^1$H NMR (CDCl$_3$) $\delta$0.88 (t, J=7 Hz, 3H), 1.08 (d, J=7 Hz, 3H), 1.40 (m, 1H), 1.61 (m, 1H), 2.13 (s, 3H), 2.42 (m, 1H). MS m/e % (chemical ionization) 101 (100, M$^+$+1). MS m/e % (electron impact) 100 (4, M$^{30}$).

EXAMPLE 23

[R]-(−)-(1-Methylpropyl)phenyl ketone was prepared from [R]-(−)-(1-methylpropyl)-3′-O-trimethylsilyl-1′-propoxyphenylborane by the method of Example 21. IR$_{\gamma max}$ 1683 cm$^{-1}$. $^1$H NMR (CDCl$_3$) $\delta$0.90 (t, J=7 Hz, 3H), 1.73 (m, 1H), 3.40 (dd, J=13 Hz, 1H), 7.43 (m, 3H), 7.90 (m, 2H). MS m/e % (chemical ionization 163 (100, M$^+$+1). MS m/e % (electron impact) 162 (5, M$^+$).

EXAMPLE 24

[S]-(+)-2,3,7-Trimethylnonan-4-one was prepared from [S]-(+)-1,2-dimethylpropyl-3′-O-trimethylsilyl-1′-isopropoxy-3″-methylbutylborane by the method of Example 21. IR$_{\gamma max}$ 1709 cm$^{-1}$. $^1$H NMR (CDCl$_3$) $\delta$0.91 (m, 12H), 1.04 (d, J=6 Hz, 3H), 1.47 (m, 2H), 1.92 (m, 1H), 1.89–2.45 (m, 3H). MS m/e % (chemical ionization 171 (100, M$^+$+1). MS m/e % (electron impact) 170 (10, M$^+$). HRMS calcd. for C$_{11}$H$_{22}$O: M=170.16706. Found: M=170.16707.

EXAMPLE 25

[R]-(+)-(1-Ethylbutyl)-3′-furyl ketone was prepared from [R]-(1-ethylbutyl)-3′-O-trimethylsilyl-1′-propoxy-3″-furylborane by the method of Example 21. IR$_{\gamma max}$ 1671 cm$^{-1}$. $^1$H NMR (CDCl$_3$) $\delta$0.90 (m, 6H), 1.23–2.33 (m, 6H), 2.87 (m, 1H), 6.73 (m, 1H), 7.40 (m, 1H). 8.00 (m, 1H). MS m/e % (chemical ionization 181 (100, M$^+$+1). Ms m/e % (electron impact) 180 (3, M$^+$). Anal. Calcd. for C$_{11}$H$_{16}$O$_2$: C, 73.30; H, 8.95. Found: C, 73.58; H, 9.03.

EXAMPLE 26

[1S,2S]-(+)-(trans-2-Methylcyclopentyl)phenyl ketone was prepared from [1S,2S]-(trans-2-methylcyclopentyl)-3′-O-trimethylsilyl)-1′-propoxyphenylborane following the method of Example 21. All spectral data are identical to the racemic compound. mp 48°-49° C. (pentane, 0° C.). Anal. Calcd. for C$_{13}$H$_{16}$O: C, 82.84; H, 8.51. Found: C, 83.07; H, 8.62.

EXAMPLE 27

[1S,2S]-(+)-(trans-2-Phenylcyclopentyl)methyl ketone was prepared by the method of Example 21 from [1S,2S]-(trans-2-phenylcyclopentyl)-3'-O-trimethylsilyl-1'-propoxymethylborane. IR$_{\gamma max}$ 1706 cm$^{-1}$. $^1$H NMR (CDCl$_3$) δ1.57–2.13 (m, 6H), 1.97 (s, 3H), 3.13 (m, 2H), 7.17 (s, 5H). MS m/e % (chemical ionization) 189 (100, M$^+$+1). MS m/e % (electron impact) 188 (41, M$^+$).

EXAMPLE 28

[1S,2S]-(+)-(trans-2-Phenylcyclopentyl)-2'-furyl ketone was prepared [1S,2S]-(trans-2-phenylcyclopentyl)-3'-O-trimethyl-silyl-1'-propoxy-2'-furylborane by the method of Example 21. mp 75°–76° C. (pentane). IR$_{\gamma max}$ (Nujol) 1660 cm$^{-1}$. $^1$H NMR (CDCl$_3$) δ1.97 (m, 6H), 3.57 (m, 2H), 6.33 (dd, J=4 Hz and 2 Hz, 1H), 7.10 (d, J=4 Hz, 1H), 7.17 (s, 5H), 7.40 (m, 1H). MS m/e % (chemical ionization 241 (100, M$^+$+1). MS m/e % (electron impact) 240 (39, M$^+$). Anal. Calcd. for C$_{16}$H$_{10}$O$_2$: C, 79.47; H, 6.21. Found: C, 79.67; H, 6.80.

EXAMPLE 29

[S]-(−)-Cyclohex-3-ene)methyl ketone was prepared from [S]-cyclohex-3-ene)methylisopropoxyborane by the method of example 21. IR$_{\gamma max}$ 1709 cm$^{-1}$. $^1$H NMR (CDCl$_3$) δ2.17 (s, 3H), 5.67 (m, 2H), $^{13}$C NMR (CDCl$_3$) δ24.54, 24.66, 26.74, 47.23, 125.26, 126.65, 211.53. MS m/e % (chemical ionization 125 (100, M$^+$+1). MS m/e % (electron impact) 124 (18, M$^+$ —CH$_3$).

EXAMPLE 30

[1S,2S]-(+)-(trans-2-Methylcyclohexyl)methyl ketone was prepared from [1S,2S]-(trans-2-methylcyclohexyl)-3'-acetoxy-1'-propoxymethylborane by the method of Example 21. IR$_{\gamma max}$ 1704 cm$^{-1}$. $^1$H NMR (CDCl$_3$) δ0.83 (d, J=6 Hz, 3H), 2.12 33.76, 34.45, 59.24, 213.05. MS m/e % (chemical ionization 141 (100, M$^+$+1). MS m/e % (electron impact) 125 (1, M$^+$ —CH$_3$).

EXAMPLE 31

[1S,2S]-(+)-(exo-2-Norbornyl)methyl ketone was prepared from [1S,2S]-(exo-2-norbornyl)-3'-O-trimethylsilyl-1'-propoxyborane by the method of Example 21. IR$_{\gamma max}$ 1706 cm$^{-1}$. $^{13}$C NMR (CDCl$_3$) δ28.73, 28.76, 29.64, 32.29, 35.88, 35.98, 39.74, 54.83, 209.76. MS m/e % (chemical ionization 139 (100, M$^+$+1). MS m/e % (electron impact) 138 (1, M$^+$). Anal. Calcd. for C$_9$H$_{18}$O: C, 78.77; H, 10.21. Found: C, 78.44; H, 10.46.

EXAMPLE 32

[1R,2R,3R,5S]-(−)-(3-Isopinocampheyl)methyl ketone was prepared from [1R,2R,3R,5S]-(3-isopinocampheyl)-3'-O-trimethylsilyl-1'-propoxymethylborane by the method of Example 21. IR$_{\gamma max}$ 1709 cm$^{-1}$. $^1$H NMR (CDCl$_3$) δ1.00 (d, J=6 Hz), 1.03 (s, 1H), 1.23 (s, 3H), 2.17 (s, 3H). MS m/e % (chemical ionization 181 (100, M$^+$+1). MS m/e % (electron impact) 180 (2, M$^{30}$ —CH$_3$).

EXAMPLE 33

Oxidations with Trimethylamine-N-oxide

The DCME reaction is carried out following the procedure described in Example 19 for the preparation of ketones. Then, instead of adding phosphate buffer, the volatiles are removed under reduced pressure. Benzene is added (5 mL), followed by water (15 mL). The flask is vigorously shaken and the organic phase is transferred via a double-ended needle to a 100 mL round-bottom flask charged with dry trimethylamine-N-oxide (45 mmol), and azeotroped in benzene for 6 h, using a magnetic stirring bar and reflux condenser. The reaction is stirred for 12 h at room temperature under a slow stream of nitrogen, diluted with diethyl ether (25 mL) and transferred to a separatory funnel containing phosphate buffer solution (150 mL). The mixture is vigorously shaken for 5 min, the phases separated, and the procedure repeated. The organic phase is washed with brine (2×25 mL), dried over MgSO$_4$, filtered, and the volatiles removed under reduced pressure. The residual oil is distilled bulb-to-bulb to provide the desired ketone (95% GC). Further purification by preparatory GC yields the analytically pure ketones.

EXAMPLE 34

Following the procedure of Example 21, [R]-(−)-2,2,4-trimethylhexan-3-one was prepared from [R]-(−)-(1-methylpropyl)-3'-O-trimethylsilyl-1'-propoxy-tert-butylborane. The reaction mixture was heated to reflux, cooled and worked up as described in Example 33. IR$_{\gamma max}$ 1702 cm$^{-1}$. $^1$H NMR (CDCl$_3$) δ0.84 (t, J=7 Hz, 3H), 1.03 (d, J=7 Hz, 3H), 1.15 (s, 9H), 1.33 (m, 1H), 1.62 (m, 1H), 2.91 (sext., J=7 Hz, 1H). MS m/e % (chemical ionization 143 (100, M$^+$+1). MS m/e % (electron impact) 142 (1, M$^+$). Anal. Calcd. for C$_9$H$_{18}$O: C, 76.06; H, 12.68. Found: C, 75.98; H, 12.86.

EXAMPLE 35

General Preparation of α-Chiral-α'-alkynyl Ketones

The preparation of [1S,2S]-(+)-1-(trans-2'-phenylcyclopentyl)-4,4,-dimethyl-2-pentyn-1-one, is typical. In a 50 mL round-bottom flask equipped with a magnetic stirring bar and a connecting tube leading to a mercury bubbler was placed 2.3 g (10 mmol) of 1S,2S-trans-2-phenyl-1-cyclopentylboronate in 10 mL of ether. To it 12.5 mmol of lithium 3,3-dimethylbutyne (prepared from 12.5 mmol of 3,3-dimethyl-1-butyne in 12.5 mL of diethyl ether and 12.5 mmol of n-butyllithium at −78° C.) was added dropwise at −78° C. The reaction mixture was stirred at −78° C. for 2 h and was quenched with 3.75 mL (4M) hydrochloric acid in diethyl ether. After 0.5 h, the reaction mixture was slowly warmed to room temperature, and the supernatant ether layer was transferred to another flask by a double-ended needle. The solid was washed with 2×10 mL of ether. The borinate ($^{11}$B NMR δ+40 ppm) thus obtained was stripped of solvent at reduced pressure. The borinate was taken up in 10 mL of diethyl ether and cooled to 0° C. To it was added 1.8 mL (20 mmol) of α,α-dichloromethyl methyl ether, followed by 20 mL (40 mmol) of lithium triethylcarboxide. After 0.5 h, the ice bath was removed and the stirring was continued for 2 h ($^{11}$B NMR 16.2). To the reaction mixture was added an excess of phosphate buffer pH 8, followed by H$_2$O$_2$. The reaction mixture was stored overnight. The organic layer was removed and the aqueous layer was extracted with 3×15 mL of ether. The combined organic layer was concentrated and the triethylcarbinol was removed under reduced pressure (1 mm). The crude residue was subjected to column chromatography to yield pure ketone, 1.73 g, 68% yield. bp 150°–155° C. (0.4 mm Hg); [α]$^{22}$D +123.24° (c, 2.08, MeOH); IR (neat) 2202, 1708, 1666 cm$^{-1}$. $^1$H NMR (CDCl$_3$) δ7.25 (s, 5H), 3.25 (m, 2H), 2.4–1.06 (m, 6H);

13C NMR (CDCl3) δ190.3, 144.1, 128.5, 127.4, 126.3, 78.9, 66.0, 61.6, 49.2, 35.8, 30.1, 29.8, 27.7, 25.4.

EXAMPLE 36

[R]-(−)-9-chloro-3-methyl-5-nonyn-4-one was prepared by the method of Example 35 from sec-butyl(5-chloro-1-pentynyl)isopropoxyborane. [α]$^{75}$D −12.84 (c 1.89, MeOH); IR (neat) 2213, 1671 cm$^{-1}$. 13C NMR (CDCl3) δ191.9, 92.2, 80.5, 50.0, 43.2, 30.5, 25.8, 16.4, 15.5, 11.4. MS m/e % (chemical ionization) 187 (100).

EXAMPLE 37

[R]-(+)-1-(2′-tetrahydrofuryl)-hept-2-yn-1-one was prepared by the method of Example 35 from [R]-(+)-1-(2′-tetrahydrofuryl)-1-hexynylisopropoxyborane. bp 77°–79° C. (0.6 mm Hg); [α]$^{25}$D +4.87° (c 0.9, MeOH); IR (neat) 2205, 1735, 1705, 1670 cm$^{-1}$. 1H NMR (CDCl3) δ3.60 , 4.16 (m, 4H), 2.50−0.73 (m, 4H), 2.50–0.73 (m, 10H); 13C NMR (CDCl3) δ69.5, 68.4, 53.0; MS m/e % (chemical ionization) 181 (100, M+H); MS m/e % (electron impact) 181 (24 M+H) 109 (100), 99 (62).

EXAMPLE 38

[R]-(+)-1-(2′-tetrahydrofuryl)-4,4-dimethyl-2-pentyn-1-one was prepared by the method of Example 35 from [R]-(+)-(2′-tetrahydrofuryl)-3,3-dimethyl-1-butynylisopropoxyborane. bp 76°–78° C. (0.6 mm Hg); [α]$^{75}$D +7.54° (c 0.49, MeOH); IR (neat) 2208, 1720, 1665 cm$^{-1}$. 1H NMR (CDCl3) δ4.20−3.60 (m, 4H), 2.50−2.00 (m, 3H), 1.20 (s, 9H); MS m/e % (chemical ionization) 181 (100, M+H); MS m/e % (electron impact) (31, M+H), 137 (39), 109 (100 ), 99 (42), 81 (79).

EXAMPLE 39

[1′S,2′S]-(+)-1-(trans-2′-(1″-furyl)-cyclopentyl)-6-chloro-2-hexyn-1-one was prepared by the method of Example 35 from [1′S,2′S]-(+)-2-(trans-2′-(1″-furyl)-cyclopentyl)-5-chloro-1-pentynylisopropoxyborane. b.p. 170°–175° C. (0.5 mm Hg); [α]$^{22}$ D +105.34° (c 2.30, MeOH); IR (neat) 2214, 1710, 1668 cm$^{-1}$. 1H NMR (CDCl3) δ7.30 (m, 1H), 6.15 (m, 12H), 3.50 (m, 2H), 2.60−1.65 (m, 6H), 1.60−0.8 (m, 6H); 13C NMR (CDCl3) δ157.1, 141.2, 110, 104.6, 92.3, 80.2, 59.0, 43.2, 41.4, 32.3, 30.5, 29.5, 25.0, 16.5; MS m/e % (electron impact) 207 (43), 266 (14), 265 (100).

EXAMPLE 40

[1′R,2′S]-(+)-1-(trans-2′-(2″-thienyl)-cyclopentyl)-2-hexyn-1-one was prepared by the method of Example 35 from [1′R,2′S]-2-(trans-2′-(2″-thienyl)-cyclopentyl)-1-pentynylisopropoxyborane. bp 145°–150° C. (0.5 mm Hg); [α]$^{22}$D +92.53 (c 2.08, MeOH); IR (neat) 2211, 1724, 1665 cm$^{-1}$. 1H NMR (CDCl3) δ7.90−6.90 (m, 3H), 3.50 (m, 1H), 2.40−1.30 (m, 5H), 1.15−0.8 (m, 7H).

As used in the above specification, the term "optically pure" refers to an enantiomeric excess of at least 99% of one of the members of an enantiomeric pair. The term "a high degree of optical purity is synonymous. The term "ee" is an abbreviation for "enantiomeric excess". The term "enantiomeric pair" refers to a pair of substances whose molecules are nonidentical mirror images.

The term "R*" refers to an optically active [(+) or (−)] substituted or unsubstituted, cyclic or acyclic (straight or branched chain) organyl group containing boron attached directly to the asymmetric center of the organyl group.

The term "simple organyl group" and "simple organyl moiety" refers to a substituted or unsubstituted acyclic or cyclic organyl group containing up to 10 carbon atoms, including, but not limited to, alkyl groups such as methyl, ethyl, isopropyl, 3-methyl-2-butyl, 2-methoxyethyl, 3-methoxypropyl, etc., cycloalkyl groups such as cyclopentyl and cyclohexyl, aromatic groups such as phenyl, toluyl, anisyl and napthyl, and glyclolic groups such as ethylene glycol, pinacol, and trimethyleneglycol, and the alkoxy derivatives into which such glycol derivatives of the "ate" complexes are transformed by treatment with acid halides or trimethylsilicon chloride, i.e. OCH2CH2OAc, OC(CH3)2C(CH3)2OAc, OCH2CH2CH2OAc, OCH2CH2OSiMe3, OC(CH3)2C(CH3)2OSiMe3, OCH2CH2CH2OSiMe3 and the like.

The processes of the present invention can be employed to prepare a wide number of optically pure borinic esters and ketones, and there are no practical limitations on the organyl groups which can be employed and synthesized in accordance with this invention.

The above description has been given by way of illustration. It will be understood by those skilled in the art that modifications may be made without departing from the spirit and scope of the claimed invention.

I claim:

1. A process for synthesizing an optically pure borinic ester represented by the formula:

R*R$^1$BOR$^2$ wherein R* is a chiral organyl moiety, R$^1$ is an aliphatic, alicyclic, aromatic, heterocyclic or alkynyl achiral moiety, and R$^2$ is an acyclic or cyclic organyl group having up to 10 carbon atoms, comprising the steps of treating an optically pure boronic ester of the formula R*B(OR$^2$)2 wherein R* and R$^2$ are as defined above, with an organyllithium compound represented by the formula R$^1$Li to form a complex, decomposing said complex with a compound selected from the group consisting of ethereal hydrogen chloride, acetyl chloride and chlorotrimethylsilane, and separating said optically pure boronic ester therefrom.

2. The process of claim 1 wherien said complex is decomposed with ethereal hydrogen chloride.

3. The process of claim 1 wherein said complex is decomposed with acetyl chloride.

4. The process of claim 1 wherein said complex is decomposed with chlorotrimethylsilane.

5. An optically pure borinic ester represented by the formula R*R$^1$BOR$^2$ wherein R* is a chiral organyl moiety, R$^1$ is an aliphatic, alicyclic, aromatic, heterocyclic or alkynyl achiral moiety and R$^2$ is an acyclic or cyclic organyl group having up to 10 carbon atoms.

6. An alkyl (1-alkynyl)borinic ester represented by the formula R(R$^1$C≡C)BOR$^2$ wherein R is an achiral alkyl moiety, R$^1$ is an achiral organyl moeity, and R$^2$ is an acyclic or cyclic organyl group having up to 10 carbon atoms.

7. A process for synthesizing an optically pure borinic ester of claim 6 comprising the steps of treating a boronic ester represented by the formula RB(OR$^2$)2 with an organyl lithium compound represented by the formula R$^1$Li and decomposing the resulting complex at −78° C. with a compound selected from the group consisting of ethereal HCl, acetyl chloride and chlorotrimethylsilane, and recovering the optically pure borinic ester therefrom.

8. An optically pure alkyl (1-alkynyl)borinic ester represented by the formula $R^*(R^1C \equiv C)BOR^2$ wherein $R^*$ is a chiral alkyl moiety, $R^1$ is an achiral organyl moiety, and $R^2$ an acyclic or cyclic organyl group having up to 10 carbon atoms.

9. A process for synthesizing an optically pure borinic ester of claim 8 comprising the steps of treating a boronic ester represented by the formula $R^*B(OR^2)_2$ with an organyl lithium compound represented by the formula $R^1Li$ and decomposing the resulting complex at $-78°$ C. with a compound selected from the group consisting of ethereal HCl, acetyl chloride and chlorotrimethylsilane, and recovering the borinic ester therefrom.

* * * * *